United States Patent [19]
McClusky

[11] Patent Number: 5,217,439
[45] Date of Patent: Jun. 8, 1993

[54] SANITARY RECTAL CATHETER AND METHOD OF USE

[76] Inventor: Kenneth D. McClusky, 10046 Springfield Cir., Davisburg, Mich. 48350

[21] Appl. No.: 895,993

[22] Filed: Jun. 8, 1992

[51] Int. Cl.⁵ ............................................. A61M 31/00
[52] U.S. Cl. .................................... 604/275; 604/163; 604/278
[58] Field of Search ............... 604/163, 171, 263, 172, 604/164, 162, 275, 278, 280

[56] References Cited

U.S. PATENT DOCUMENTS 3,894,540  7/1975  Bonner, Jr. .......................... 604/171
4,419,099  12/1983  Miller .................................. 604/275
4,772,275  9/1988  Erlich ............................. 604/263 X
4,842,580  6/1989  Ouelette ......................... 604/275 X Primary Examiner—John D. Yasko
Attorney, Agent, or Firm—Krass & Young

[57] ABSTRACT

A sanitary catheter particularly designed for the administration of barium enemas. The catheter includes a protective sheath formed of a fluid-impervious, flexible material, which may be extended over those portions of the catheter which have been inserted into a patient so that the sheath completely encloses contaminated portions of the catheter to prevent leakage of contaminated fluids therefrom.

13 Claims, 1 Drawing Sheet

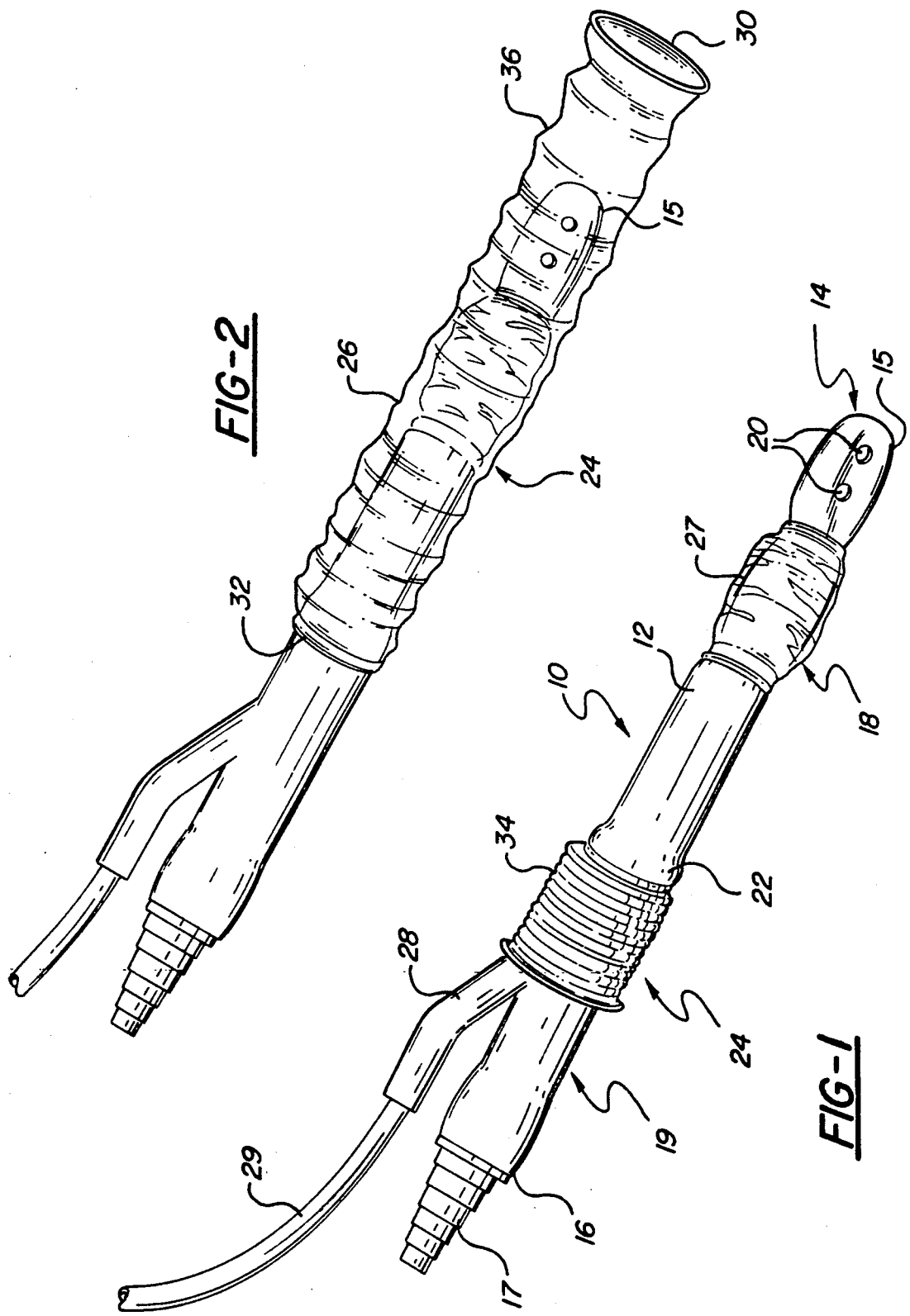

SANITARY RECTAL CATHETER AND METHOD OF USE

FIELD OF THE INVENTION

This invention concerns the field of catheters insertable into a body orifice to dispense fluid thereinto and, more particularly, to catheters used for the administration of fluids for radiographic studies.

DESCRIPTION OF THE RELEVANT PRIOR ART

In preparing a patient for radiographic diagnostic studies of the lower gastrointestinal tract, it is conventional to administer a "barium enema" contrast medium to the patient. Typically, the radiographic fluid is introduced into the patient's GI tract by means of rectal injection. A catheter having an appropriately configured cannula disposed at a forward end thereof is inserted into the patient's rectum. The catheter is connected to a source of radiographic fluid (such as a solution of various barium salts and inert materials) and the liquid is caused to flow through the catheter and cannula into the patient's rectum, typically either via gravity feed or injection under pressure. Optionally, gas bubbles may also be introduced into the liquid for the performance of particular radiographic studies.

Following the x-ray examination of the colon, the catheter is removed from the patient's rectum. Of course, even though the flow of fluid has been stopped, some fluid remains within the catheter. Furthermore, the patient's own intestinal fluids will have mixed with the radiographic fluid and will generally be present inside the catheter after it is removed. Frequently, removal of the catheter causes some of the radiographic fluid contaminated with body fluids to splash onto medical personnel in charge of the procedure, particularly the radiographic technologist. Obviously, splashing of this contaminated fluid onto medical personnel is not only highly undesirable from an aesthetic viewpoint, but can expose them to the risk of contracting numerous infectious diseases, including AIDS and hepatitis.

There are a number of patents relating to covers for protecting enema dispenser tips prior to use. See, for example, U.S. Pat. Nos.: 3,234,945; 3,486,503; 3,882,866; and 4,752,288. However, none of these references discuss the problem of covering used dispensers. Clearly, the need for covering the tip of the enema dispenser after use is just as acute as protecting it prior to use.

There is a need for a catheter which may be easily and effectively sheathed in protective material after it has been removed from a patient. There is a particular need for such a catheter including a protective shield which is inexpensive, simple to manufacture, does not interfere with the normal use of the catheter, and is, itself, quick and easy to use.

SUMMARY OF THE INVENTION

Disclosed and claimed herein is an improved radiographic enema catheter having its own self-contained protective shield. The catheter body is of a conventional type comprising an elongated tube having first and second ends and forward and rearward portions disposed proximate, respectively, said first and second ends. A rectal cannula is formed on the first end of the tube and is configured for easy insertion into the rectum of a patient undergoing radiographic studies of the lower gastrointestinal tract. The cannula includes a plurality of bores formed therethrough for passage of a radiographic fluid into the rectum. Means are provided on the second end of the tube for attaching the tube to a source of the radiographic liquid so that the liquid may flow through the tube, the cannula and the bores into the patient's rectum.

Conventionally, a stop is formed on the tube medial of the forward and rearward portions for engagement with the anal sphincter area of the patient. Typically, the stop comprises one or more enlarged areas or "bumps" formed on the tube. The stop acts to prevent the technician from inserting too much of the length of the tube into the patient's rectum.

The catheter of the prevent invention further includes a shield for enclosing the forward portion of the tube. The shield is disposed around the tube at a location rearward of the stop. Preferably, the shield is in the form of a tubular sheath having first and second open ends and formed of a liquid-impervious, flexible material. The first end of the sheath is attached to the tube behind the stop, and the second end is left free. The length of the sheath is sufficient to extend beyond the first end of the tube such that, when the sheath is extended, it encloses the cannula and forward portion of the tube. Preferably, its length is sufficient to include a portion which extends beyond the first end for a sufficient distance to permit the second, open end to be closed by twisting the sheath, or some other means. When not in use, the sheath is disposed so that it overlies the rearward portion of the catheter to leave it unobstructed while it is in use.

Prior to being used to enclose the end of a used catheter, the length of the protective sheath may simply be left to hang loosely around the rearward portion of the catheter. In some instances it is desirable to minimize this length of shield so that the possibility of it obstructing the forward portion of the catheter is reduced. This may be accomplished by rolling the length of the sheath onto itself, but a rolled sheath is somewhat awkward to use. Preferably, the sheath is provided with circumferentially disposed accordion pleats. Before use, the sheath accordion pleats onto itself. When in use, the pleats are extended by simply pulling the free end of the sheath.

A method of using the sanitary catheter of the present invention is also described.

BRIEF DESCRIPTION OF THE DRAWINGS

The following detailed description is best understood by reference to the following drawing in which:

FIG. 1 is a perspective view of the sanitary catheter of the present invention prior to employment of the protective sheath; and FIG. 2 shows the sanitary catheter of FIG. 1 with the sheath in its extended position.

DETAILED DESCRIPTION OF THE PREFERRED EMBODIMENTS

Throughout the following detailed description, identical reference numerals are used to show the same element of the invention shown in multiple figures thereof. Referring now to the drawings, and in particular to FIG. 1, there is shown a sanitary catheter 10 constructed according to the principles of the present invention. The catheter 10 includes an elongated tube 12 having first and second ends 14,16 and forward and rearward portions 18,19 proximate, respectively, the first and second ends 15,16. Typically, the tube 12 is formed of a soft, polymeric material, such as rubber, polyvinylchloride or other suitable material. It is necessary that the material of which tube 12 is fabricated be somewhat resilient and deformable to accommodate anatomical variations among patients.

Disposed at the first end 14 of tube 12 is a rectal cannula 15. Cannula 15 is configured for insertion into the rectum of a patient, and includes a plurality of bores 20 formed therethrough for passage of a radiographic fluid through the cannula and bores and into the rectum. Two such bores 20 are shown in FIG. 1, but it is to be understood that other bores may be provided, such as in the tip end of cannula 15 as well as on other portions thereof not visible in the Figure. The particular number and arrangement of bores is not considered material to the practice of the present invention.

Disposed at the second end 16 of tube 12 is a means 17 for attaching the tube 12 to a source of radiographic fluid (not shown), such as a liquid suspension and/or solution of barium salts and other inert ingredients. As depicted in FIG. 1, the attaching means 17 is in the form of a tube connector which is insertable into the end of plastic tubing (such as PVC tubing) of a variety of standard gauges. By this means, the radiographic fluid is permitted to flow through tube 12, cannula 15, bores 20 and into the rectum and intestinal tract of the patient. Typically, the flow of the fluid is adjustable by various valves, and may be assisted by gravity or positive pressure means.

A stop 22 is formed on the tube 12 at a location medial of said first and second ends 14,16. The stop 22 is designed for engagement with the rectal sphincter area of a patient so that the tube will not accidentally be inserted too far into the patient's rectum, which could cause perforation or other damage. As depicted in FIGS. 1 and 2, the stop 22 is in the form of a plurality of radially disposed "bumps," although other designs may be used.

The catheter of the present invention, as is known in the prior art, also includes an inflatable cuff 27 in communication with a source of air or other gas (not shown) via branch 28 which is attachable to flexible tubing 29. Typically, after the cannula is correctly positioned in the rectum, the cuff 27 is inflated so as to help prevent escapage of radiopaque fluid from the rectum.

Disposed around tube 12 behind stop 22 is a protective shield 24 designed to enclose the forward portion 18 and cannula 15 of the catheter of the present invention. As can be seen most clearly in FIG. 2, which depicts the shield 24 in its extended position, the shield 24 comprises tubular sheath 26 having first and second open ends 30,32. Second open end 32 is attached to tube 12 (by wrapping with thread, by a suitable adhesive or any other means) whereas first open end 30 is left free. As can be seen in FIG. 2, (showing the sheath 26 in its extended position), the length of tubular sheath 26 is great enough that the sheath 26 extends beyond first end 15 for a sufficient distance to define a portion 36 long enough to be closed by twisting, or some other means.

The tubular sheath 26 is formed of a liquid-impervious, flexible material such as films of latex, polyvinylchloride, polyurethane, polyvinylidine fluoride etc. Ideally, the film should be thin enough so that the sheath 26 is very flexible and occupies as little space as possible, but thick enough so that the material is liquid-impervious. It should also be compatible with, and not break down in reaction to, any lubricant used on the cannula 15.

Before the catheter of the present invention is used, the protective shield 24 is carried in a retracted position on the rearward portion 19 of the tube 12, as can be seen in FIG. 1. It may be simply carried loosely thereon, or a series of circumferential, accordion pleats 34 may be formed in tubular sheath 26 so that the sheath will lie in neat folds when in its retracted position and will present no obstruction to using the catheter 10. If necessary, means may be provided (not shown) for fastening the unattached portions of sheath 26 to tube 12 when the sheath is not in use.

The sanitary catheter 10 of the present invention may be used for the administration of radiographic liquid in an entirely conventional manner. That is, after the patient is suitably prepared, the forward portion 18 of the device is inserted in to the rectum. Typically, the catheter will be provided with a suitable lubricant for this purpose. The catheter 10 is inserted to a sufficient depth for cannula 15 to be disposed in that portion of the rectum closest to the remainder of the gastrointestinal tract. Stop 22 will prevent the catheter 10 from being inserted too deeply. Flow of the radiographic fluid is started through the device and the inflatable cuff is inflated to prevent the escape thereof. After sufficient fluid has been inserted into the GI tract in this manner, and the radiological studies completed, the flow of the fluid is stopped, the cuff deflated, and the catheter is removed from the patient's rectum.

It is then a very simple matter for the medical personnel to hold the rearward portion 19 of the catheter 10 in one hand and grasp the first, free end 30 of the tubular sheath 26 in the other hand. The sheath 26 is then pulled from the retracted position shown in FIG. 1 to the extended position shown in FIG. 2, wherein the front portion 18 and cannula 15 are completely surrounded by the sheath 26. The technician then simply twists the extended portion 36 of sheath 26 to close and seal off the shield 24. The sheath 26 will then completely and sanitarily enclose the entirety of those portions of the catheter 10 which have been inside the patient, as well as those portions (particularly bores 20) which normally leak contaminated fluid. After disconnecting the catheter from the air and fluid lines, it is simply discarded.

Since the forward portion 18 of the catheter 10 is completely and easily enclosed within the protective sheath 24 immediately after the catheter is removed from the patient, the possibility of contamination of medical personnel with contaminated fluids is either greatly minimized or completely eliminated. While a complete enclosure of the contaminants may be made by simply twisting extended portion 36 of sheath 26, for further and additional protection, it may be desirable to tie off or otherwise seal the sheath with tape, flexible wire, etc.

The sanitary catheter of the present invention has been described with reference to particular embodiments and exemplifications thereof. It is to be understood that the present invention may be employed in combination with catheters of designs other than those depicted herein. Variation in design of some of the elements thereof may occur to one skilled in the art without departing from the scope of the present invention. The scope of the present invention is not intended to be limited to the embodiments and exemplifications depicted herein, but solely by the claims appended hereto and all equivalents thereof.

I claim:

1. A sanitary catheter comprising:
   an elongated tube having first and second ends and forward and rearward portions disposed proximate, respectively, said first and second ends;
   a rectal cannula disposed proximate said first end, said cannula being configured for insertion into the rectum of a patient and including a bore formed therethrough for passage of a radiographic liquid into the rectum;
   means disposed proximate said second end for attaching said tube to a source of said radiographic liquid for flow of said liquid through said tube, said cannula and said bore;
   a stop formed on said tube medial of said forward and rearward portions for engagement with the anal sphincter of the patient so that only said forward portion of said tube can be inserted into the rectum; and
   a shield for enclosing the forward portion of said tube, said shield being disposed around said tube at a location rearward of said stop, said shield including a liquid-impervious, flexible sheath having an inner surface adjacent said tube and an outer, exposed surface and being of a length sufficient to extend beyond said first end to enclose said cannula and said forward portion such that said inner surface is exposed, said sheath, when not in use, overlying said rearward portion.

2. The catheter of claim 1 further comprising an inflatable cuff disposed around said tube on said forward portion at a location rearward of said cannula to act as a barrier against leakage of said fluid from the rectum.

3. The catheter of claim 1 wherein the sheath further includes first and second open ends, said first end being disposed coaxially around said tube and attached thereto, said first end remaining free of said tube.

4. The catheter of claim 3 wherein the sheath further includes a plurality of circumferentially extending pleats such that said free, second end lies proximate said first end when the shield is not in use.

5. The catheter of claim 3 wherein said shield length is sufficient to provide a portion that extends beyond said tube first end so that the second, open end of the sheath may be sealed.

6. The catheter of claim 1 wherein the sheath is formed of a material selected from the group consisting of: latex; polyvinylchloride; polyurethane; polyvinylidine fluoride; and mixtures thereof.

7. A protective shield for enclosing a forward portion of a barium enema catheter of the type including an elongated tube having:
   first and second ends and forward and rearward portions disposed proximate, respectively, said first and second ends; a rectal cannula disposed proximate said end and configured for insertion into the rectum of a patient, said cannula including a bore formed therethrough for passage of radiographic fluid into the rectum; means proximate said second end for attaching said tube to a source of radiographic liquid for flow of said liquid through said tube, said cannula, and said bore; and a stop formed on said tube medial of said forward and rearward portions for engagement with the anal sphincter of said patient, such that only said forward portion of said tube can be inserted into the rectum, said sheath comprising:
   a liquid-impervious, flexible sheath disposed around said tube at a location rearward of said stop and having an inner surface adjacent said tube and an outer exposed surface, said sheath having a length sufficient to extend beyond said first end to enclose said cannula and said forward portion such that said inner surface is exposed, said sheath, when not in use, overlying said rearward portion.

8. The catheter of claim 7 further comprising an inflatable cuff disposed around said tube on said forward portion at a location rearward of said cannula to act as a barrier against leakage of said fluid from the rectum.

9. The catheter of claim 7 wherein the sheath further includes first and second open ends, said first end being disposed coaxially around said tube and attached thereto, said first end remaining free of said tube.

10. The catheter of claim 9 wherein the sheath further includes a plurality of circumferentially extending pleats such that said free, second end lies proximate said first end when the shield is not in use.

11. The catheter of claim 9 wherein said shield length is sufficient to provide a portion that extends beyond said tube first end so that the second, open end of the sheath may be sealed.

12. The catheter of claim 7 wherein the sheath is formed of a material selected from the group consisting of: latex; polyvinylchoride; polyurethane; polyvinylidine fluoride; and mixtures thereof.

13. A method of protectively enclosing a barium enema catheter after it has been used in a patient, said method comprising the steps of:
   providing a catheter including
      an elongated tube having first and second ends and forward and rearward portions disposed proximate, respectively, said first and second ends;
      a rectal cannula disposed proximate said first end, said cannula being configured for insertion into the rectum of a patient and including a bore formed therethrough for passage of a radiographic liquid into the rectum;
      means disposed proximate said second end for attaching said tube to a source of said radiographic liquid for flow of said liquid through said tube, said cannula and said bore;
      a stop formed on said tube medial of said forward and rearward portions for engagement with the anal sphincter of the patient so that only said forward portion of said tube can be inserted into the rectum; and
      a shield for enclosing the forward portion of said tube, said shield being disposed around said tube at a location rearward of said stop, said shield including a liquid-impervious, flexible sheath having an inner surface adjacent said tube and an outer exposed surface and being of a length sufficient to extend beyond said first end to enclose said cannula and said forward portion such that said inner surface is exposed, said sheath, when not in use, overlying said rearward portion;
   attaching said catheter to said source of radiographic fluid;
   inserting the cannula into the patient's rectum;
   causing the radiographic fluid to flow through said tube, cannula, bore and into the rectum for a sufficient time to enable radiographic studies of the patient's lower gastrointestinal tract to be done;
   stopping the flow of said radiographic fluid;
   removing said cannula from the patient's rectum;
   grasping the free end of the sheath;
   bringing the free end of the sheath forward until the sheath is fully extended and its inner surface exposed;
   closing the free end to enclose the cannula and forward portion inside said sheath; and
   disposing of said catheter.

* * * * *